United States Patent [19]

Sanchez et al.

[11] 4,219,676
[45] Aug. 26, 1980

[54] UNSYMMETRICAL DIPEROXIDES AND PROCESSES OF USE IN POLYMERIZING UNSATURATED MONOMERS

[75] Inventors: Jose Sanchez, Grand Island; Vasanth R. Kamath, Tonawanda, both of N.Y.; James C. Halas, Chicago, Ill.

[73] Assignee: Pennwalt Corporation, Philadelphia, Pa.

[21] Appl. No.: 869,411

[22] Filed: Jan. 16, 1978

Related U.S. Application Data

[62] Division of Ser. No. 757,185, Jan. 6, 1977, Pat. No. 4,079,074.

[51] Int. Cl.$^2$ ............................................. C07C 179/14
[52] U.S. Cl. ............................... 568/566; 260/453 RZ; 260/463; 560/127
[58] Field of Search ........ 260/610 D, 610 R, 453 RZ, 260/463; 568/566; 560/127

[56] References Cited

U.S. PATENT DOCUMENTS

| 3,706,818 | 12/1972 | Mageli et al. | 260/610 D |
|---|---|---|---|
| 4,079,074 | 3/1978 | Sanchez et al. | 260/453 RZ |

FOREIGN PATENT DOCUMENTS 43-18527  8/1968  Japan .................................. 260/610 D

OTHER PUBLICATIONS

Sosnovsky, et al., J. Organic Chem., vol. 25, pp. 899–903 (1960).

*Primary Examiner*—Werren B. Lone

[57] ABSTRACT

Unsymmetrical diperoxides of the general structure:

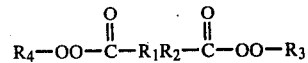

for example, 4-(t-butylperoxycarbonyl)-3-hexyl-6-[7-(tbutylperoxycarbonyl)heptyl] cyclohexene, are useful for polymerizing ethylenically unsaturated monomers (such as styrene). The polymerizations can be carried out at higher temperatures and in shorter times than with conventional initiator systems, without detrimental decrease in polymer molecular weight or significant change in molecular weight distribution. The unsymmetrical diperoxides are also useful as catalysts for curing unsaturated polyester resins.

5 Claims, No Drawings

UNSYMMETRICAL DIPEROXIDES AND PROCESSES OF USE IN POLYMERIZING UNSATURATED MONOMERS

This is a division of application Ser. No. 757,185, filed Jan. 6, 1977, now U.S. Pat. No. 4,079,074.

BACKGROUND OF THE INVENTION

It is known that one can increase the capacity of a PVC reactor by maintaining the temperature of the polymerization system constant and using more active free-radical initiator. However, since the molecular weight of PVC is determined to a great extent by temperature the molecular weight of the product will not be increased by use of a more active free-radical initiator used under the same temperature conditions. Furthermore, in the case of styrene polymerizations, use of a more active free radical initiator results in a decrease in molecular weight under the same polymerization conditions. If the temperature of the system is increased at constant initiator concentration the rate of polymerization will increase but the molecular weight will decrease. A significant change in polystyrene molecular weight causes changes in the physical properties of the resulting polystyrene. The compounds of the present invention provide an increased rate of polymerization without loss of polymer properties.

STATEMENT OF THE INVENTION

This invention relates to a compound of the structure

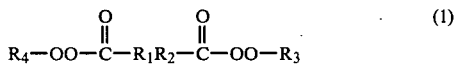
$$R_4-OO-\overset{O}{\underset{\|}{C}}-R_1R_2-\overset{O}{\underset{\|}{C}}-OO-R_3 \qquad (1)$$

where $R_1$ is a substituted or an unsubstituted cyclohexylene or cyclohexenylene diradical, $F_2$ is an alkylene diradical of 7 to 11 carbons, alkenylene diradical of 9 to 11 carbons and alkadienylene diradical of 11 carbons. Substituents for $R_1$ can be one or more alkyl radicals of 1 to 6 carbons, alkenyl radicals of 4 to 6 carbons, alkadienyl radicals of 6 carbons, —C(O)OOR, and —C(O)OOR$_3$ or carboxy. $R_3$ and $R_4$ are substituted or unsubstituted t-alkyl radicals of 4 to 12 carbons, t-cycloalkyl radicals of 6 to 13 carbons, t-alkynyl radicals of 5 to 8 carbons or t-aralkyl radicals of 9 to 13 carbons. $R_3$ and $R_4$ are also substituted or unsubstituted acyl radicals of 1 to 18 carbons, alkenoyl radicals of 3 to 11 carbons, alkadienoyl radicals of 6 carbons, aroyl radicals of 7 to 11 carbons, alkoxycarbonyl radicals of 2 to 19 carbons and cycloalkoxycarbonyl radicals of 6 to 13 carbons. Substituents for $R_3$ and $R_4$ can be lower alkyl, chloro, hydroxy, acyloxy, aroyloxy, alkoxycarbonyloxy, and t-alkylperoxy. $R_3$ and $R_4$ can be the same or different. These compounds are useful as initiators for polymerizing ethylenically unsaturated monomers and as curing catalysts for curing of unsaturated polyester resin compositions.

FURTHER DESCRIPTION OF THE INVENTION

Compounds of the present invention can be prepared from the corresponding unsymmetrical diacids via reaction of the unsymmetrical diacid chloride intermediate with a hydroperoxide or a peroxy acid in the presence of a base. They can be employed for polymerizing monomers (such as styrene) to polymers, at higher temperatures and in shorter times than currently in common use without at the same time decreasing molecular weight or changing polymer molecular weight distributions. They are also useful for curing unsaturated polyester resins, for polymerizing methyl methacrylate (MMA) to higher molecular weight polymers or for polymerizing MMA to the same molecular weight polymers (as with conventional initiators) but over a shorter time period and at higher temperatures, and for polymerizing styrene in the presence of a butadiene-based elastomer or in the presence of another type of elastomer to produce high impact polystyrene.

PREPARATION OF COMPOUNDS (1)

Diacids useful for the preparation of the novel unsymmetrical diperoxyester and di(diacylperoxide) compositions of this invention are diacids which contain a cyclohexene ring. These acids are prepared using the Diels Alder reaction. The diene is a long chain di-or polyunsaturated carboxylic acid such as linoleic acid (9,12-octadecadienic acid), linolenic acid (9,12,15-octadecatrienic acid) or eleostearic acid (9, 11, 13-octadecatrienic acid) whereas the dienophile is an unsaturated acid (or acid anhydride) such as acrylic acid, methacrylic acid, fumaric acid, maleic acid or maleic anhydride. Apparently, the unconjugated di- and polyunsaturated long chain acids are isomerized to the conjugated forms prior to reaction with the dienophile. For example, linoleic acid isomerizes to a mixture of 9,11- and 10,12-octadecadienic acids prior to reaction with the dienophile. Treatment of linoleic acid with acrylic acid in this manner has been employed commercially to produce a mixture of 3-hexyl-4-carboxy-6-(7-carboxyheptyl)cyclohexene, 3-hexyl-5-carboxy-6-(7-carboxyheptyl)cyclohexene, 3-pentyl-4-carboxy-6-(8-carboxyoctyl)cyclohexene and 3-pentyl-5-carboxy-6-(8-carboxyoctyl)cyclohexene. Such acid mixtures have been employed in industrial cleaner formulations.

The above diacids can be hydrogenated to the saturated diacid analogs using conventional catalytic hydrogenation techniques. These saturated diacids contain a cyclohexane ring. The saturated analogues of the diacids mentioned above can be produced in this manner.

The diacids are converted to the intermediate diacid chlorides by treatment with acid chlorinating agents such as PCl$_3$, POCl$_3$, PCl$_5$, SOCl$_2$, phosgene and benzotrichloride and the diacid chlorides are subsequently treated with monohydroperoxides or monoperoxyacids in the presence of a base to produce (1). In an aqueous medium suitable bases include KOH and NaOH while in an anhydrous medium trialkylamine bases such as triethylamine, N,N-dimethylaniline, 1,4-diazabicyclo [2.2.2] octane or pyridine can be employed. Solvents such as pentane, hexane, heptane, isooctane, odorless mineral spirits, benzene, toluene, diethyl ether, methylene chloride or ethyl acetate can be optionally used for the peroxidation reaction as well as for product isolation.

The monohydroperoxides which are useful for producing the compounds of this invention are t-alkyl hydroperoxides such as t-butyl hydroperoxide, t-amyl hydroperoxide, 1,1-dimethylbutyl hydroperoxide, 1-ethyl-1-methylpropyl hydroperoxide, 1,1,3,3-tetramethyl butyl hydroperoxide, 1,1-dimethyldecyl hydroperoxide, 2-chloro-1,1-dimethylethylhydroperoxide, 3-hydroxy-1,1-dimethylbutyl hydroperoxide, 2-hydroxy-1,1-dimethylethyl hydroperoxide, 3-acetoxy-1,1-dimethylbutyl hydroperoxide, 3-benzoyloxy-1,1- dimethylbutyl hydroperoxide, 3-isopropoxycarbonyloxy-1,1-dimethylbutyl hydroperoxide, 1,1,4,4,-tetramethyl-4-(t-butylperoxy)-butyl hydroperoxide and paramenthane hydroperoxide; t-cloalkyl hydroperoxides such as 1-methylcyclopentyl hydroperoxide, 1-methylcyclohexyl hydroperoxide, 1-methylcyclododecyl hydroperoxide and 1-ethynylcyclohexyl hydroperoxide; t-alkynyl hydroperoxides such as 2-methyl-2-hydroperoxy-3-butyne, 3-methyl-3-hydroperoxy-1-pentyne and 3-methyl-3-hydroperoxy-1-heptyne; and t-aralkyl hydroperoxides such as alpha-cumyl hydroperoxide (cumene hydroperoxide), p-methyl-alpha-cumyl hydroperoxide, m-isopropyl-alpha-cumyl hydroperoxide and p-isopropyl-alpha-cumyl hydroperoxide.

The monoperoxyacids which are useful for producing the compounds of this invention are peroxyformic acid, peroxyacetic acid, peroxyhexanoic acid, peroxychloroacetic acid, peroxylauric acid, peroxystearic acid, peroxyacrylic acid, peroxycrotonic acid, peroxyundecylenic acid, peroxyhexadienoic acid, peroxybenzoic acid, peroxy-m-chlorobenzoic acid, peroxy-o-toluic acid, peroxy-4-t-butylbenzoic acid, peroxynaphthoic acid, peroxyisobutyric acid, peroxy-2-ethylhexanoic acid, peroxypivalic acid, hydroperoxycarbonylcyclohexane and peroxyneodecanoic acid. Such monoperoxyacids can be prepared by either reacting the corresponding carboxylic acid with $H_2O_2$ in the presence of of a strong acid (e.g., $H_2SO_4$, $H_3PO_4$, methylsulfonic acid, trifluoroacetic acid, etc.) or by reacting the corresponding acid chloride, bromide or anhydride with excess alkaline $H_2O_2$ followed by acidification.

Alternately, the unsymmetrical di(diacyl peroxides) can be prepared by reacting an unsymmetrical diperoxyacid with one or more acid chlorides or chloroformates in the presence of a base.

The diacids described above can be converted to the unsymmetrical diperoxyacids by either reacting the diacids with $H_2O_2$ in the presence of a strong acid (e.g., $H_2SO_4$, $H_3PO_4$, methylsulfonic acid, trifluoroacetic acid, etc.) or by reacting the corresponding unsymmetrical diacid chlorides with excessive alkaline $H_2O_2$ followed by acidification.

Typical of the novel unsymmetrical diperoxyesters of the present invention are: 4- and 5-(t-butylperoxycarbonyl)-3-hexyl-6-[7-(t-butylperoxycarbonyl)heptyl]cyclohexenes, 4-(t-butylperoxycarbonyl)-3-hexyl-4-methyl-6-[7-(t-butylperoxycarbonyl)heptyl]cyclohexene, 5-(t-butylperoxycarbonyl)-3-hexyl-5-methyl-6-[7-(t-butylperoxycarbonyl)heptyl]) cyclohexene, 4- and 5-(t-butylperoxycarbonyl)-3-pentyl-6-[8-(t-butylperoxycarbonyl)octyl]cyclohexenes, 4-(t-butylperoxycarbonyl)-4-methyl-3-pentyl-6-[8-(t-butylperoxycarbonyl)octyl]cyclohexene, 5-(t-butylperoxycarbonyl)-5-methyl-3-pentyl-6-[8-(t-butylperoxycarbonyl)octyl]cyclohexene, 4,5-di-(t-butylperoxycarbonyl)-3-hexyl-6-[7-(t-butylperoxycarbonyl)heptyl]cyclohexene, 4,5-di-(t-butylperoxycarbonyl)-3-pentyl-6-[8-(t-butylperoxycarbonyl)octyl]cyclohexene, 4-(t-butylperoxycarbonyl)-3-(3-hexenyl)-6-[7-(t-butylperoxycarbonyl)heptyl]cyclohexene, 4-(t-butylperoxycarbonyl)-3-(2-pentenyl)-6-[8-(t-butylperoxycarbonyl)octyl]cyclohexene, 4-(t-butylperoxycarbonyl)-3-ethyl-6-[11-(t-butylperoxycarbonyl)-3-undecenyl]cyclohexene, 4-(t-butylperoxycarbonyl)-3-propyl-6-[10-(t-butylperoxycarbonyl)-2-decenyl]cyclohexene, 4-(t-butylperoxycarbonyl)-3-butyl-6-[9-(t-butylperoxycarbonyl-1-nonenyl]cyclohexene, 4-(t-butylperoxycarbonyl)-3-(1-hexenyl)-6-[7-(t-butylperoxycarbonyl)heptyl]cyclohexene, 4-(t-butylperoxycarbonyl)-3-ethyl-6-[11-(t-butylperoxycarbonyl)-1,3-undecadienyl]cyclohexene, 4-(t-butylperocycarboryl)-3-(1-butenyl-6-[9-(t-butylperoxycarbonyl)-1-nonenyl]-cyclohexene, 4-(t-butylperoxycarbonyl)-3-(1,3-hexadienyl)-6-[7-(t-butylperoxycarbonyl)heptyl]cyclohexene, 2-(t-butylperoxycarbonyl)-1-hexyl-4-[7-(t-butylperoxycarbonyl)heptyl]cyclohexane, 3-(t-butylperoxycarbonyl-1-hexyl-4-[7-(t-butylperoxycarbonyl)heptyl]cyclohexane, 2-(t-butylperoxycarbonyl)-1-hexyl-2-methyl-4-[7-butylperoxycarbonyl)heptyl) cyclohexane, 3-(t-butylperoxycarbonyl)-1hexyl-3-methyl-4-[7-(t-butyulperoxycarbonyl)heptyl]cyclohexane, 2-(t-butylperoxycarbonyl)-1-pentyl-4-[8-(t-butylperoxycarbonyl)octyl] cyclohexane, 3-(t-butylperoxycarbonyl)-1-pentyl-4-[8-(t-butylperoxycarbonyl(octyl]cyclohexane, 2-(t-butylperoxycarbonyl)-2-methyl-1-pentyl-4-[8-(t-butylperoxycarbonyl)octyl]cyclohexane, 3-(t-butylperoxycarbonyl)-3-methyl-1-pentyl-4-[8-(t-butylperoxycarbonyl)octyl]cyclohexane, 2,3-di-(t-butylperoxycarbonyl)-1-hexyl-4-[7-(t-butylperoxycarbonyl)heptyl]cyclohexane, 2,3-di-(t-butylperoxycarbonyl)-1-pentyl-4-[8-(t-butylperoxycarbonyl)octyl]cyclohexane, 2-(t-butylperoxycarbonyl)-1-ethyl-4-[11-(t-butylperoxycarbonyl)undecyl]cyclohexane, 2-(t-butylperoxycarbonyl)-1-propyl-4-[10-(t-butylperoxycarbonyl)decyl]cyclohexane, 2-(t-butylperoxycarbonyl)-1-butyl-4-[9-(t-butylperoxycarbonyl)nonyl]cyclohexene, 4- and 5-(t-amylperoxycarbonyl)-3hexyl-6-[7-(t-amylperoxycarbonyl)heptyl]cyclohexenes, 4- and 5-(t-amylperoxycarbonyl)-3-pentyl-6-[8-(t-amylperoxycarbonyl)octyl]cyclohexenes, 4- and 5-(1,1,3,3-tetramethylbutyl)peroxycarbonyl-3-hexyl-6-[7-(1,1,3,3-tetramethylbutyl)-peroxycarbonylheptyl]cyclohexenes, 4- and 5-(1,1,3,3-tetramethylbutyl)peroxycarbonyl-3-pentyl-6-[8-(1,1,3,3-tetramethylbutyl)peroxycarbonyloctyl] cyclohexenes, 4- and 5-(alpha-cumylperoxycarbonyl)-3-hexyl-6-[7-(alpha-cumulyperoxycarbonyl)heptyl]cyclohexenes, 4- and 5-(alpha-cumylperoxycarbonyl)-3-pentyl-6-[8-(alpha-cumylperoxycarbonyl)octyl]cyclohexenes, 4- and 5-[1,1,4,4-tetramethyl-4-(t-butylperoxy)butyl]peroxycarbonyl-3-hexyl-6-[7-(1,1,4,4-tetramethyl-4-(t-butylperoxy)butyl)peroxycarbonylheptyl]cyclohexenes, 4- and 5-[1,1,4,4-tetramethyl-4(t-butylperoxy)butyl]peroxycarbonyl-3-pentyl-6-[8-(1,1,4,4-tetramethyl-4-(t-butylperoxy)butyl)peroxycarbonyloctyl]cyclohexenes, 4- and 5-(3-hydroxy-1,1-dimethylbutyl)peroxycarbonyl-3-hexyl-6[7-(3-hydroxy-1,1-dimethylbutyl)peroxycarbonylheptyl]cyclohexenes, 4- and 5-(3-hydroxy-1,1-dimethylbutyl)peroxycarbonyl-3-pentyl-6-[8-(3-hydroxy-1,1-dimethylbutyl)peroxycarbonyloctyl]cyclohexenes, 4-(t-butylperoxycarbonyl)-3-hexyl-6-[7-(t-amylperoxycarbonyl)heptyl]cyclohexene, 4-(t-amylperoxycarbonyl)-3-hexyl-6-[7-(t-butylperoxycarbonyl)heptyl]cyclohexene, 2-(t-amylperoxycarbonyl)-1-hexyl-4-[7-(t-amylperoxycarbonyl)heptyl]cyclohexane, 3-(t-amylperoxycarbonyl)-1-hexyl-4-[7-(t-amylperoxycarbonyl)heptyl]cyclohexane, 2-(t-amylperoxycarbonyl)-1-pentyl-4-[8-(t-amylperoxycarbonyl)octyl]cyclohexane, 3-(t-amylperoxycarbonyl-1-pentyl-4-[8-(t-amylperoxycarbonyl)octyl]cyclohexane, 2,3-di-(t-amylperoxycarbonyl)-1-hexyl-4-[7-(t-amylperoxycarbonyl)heptyl]cyclohexane, 2,3-di-(t-amylperoxycarbonyl)-1-pentyl-4-[8-(t-amylperoxycarbonyl)octyl]cyclohexane, 2,3-di-(alpha-cumuylperoxycarbonyl)-1-hexyl-4-[7-(alpha-cumylperoxycarbonyl)heptyl]cyclohexane, 2,3-di-[1,1,3,3-tetramethylbutyl)peroxycarbonyl]-1-hexyl-4-[7-(1,1,3,3-tetramethylbutyl)-peroxycarbonylheptyl] cyclohexane, 2,3-di-[(1,1,4,4-tetramethylbutyl-4-(t-butylperoxy)butylperoxycarbonyl]-1-hexyl-4[7-(1,1,4,4-tetramethylbutyl-4-(t-butylperoxy)-butyl)peroxycarbonylheptyl]cyclohexane, 4-(t-butylperoxycarbonyl)-5-carboxy-3-hexyl-6-[7-(t-butylperoxycarbonyl)heptyl]cyclohexene, 4-(t-butylperoxycarbonyl-5-carboxy-3-pentyl-6-[8-(t-butylperoxycarbonyl)octyl]cyclohexene, 5-(t-butylperoxyperoxycarbonyl)-4-carboxy-3-hexyl-6-[7-(t-butylperoxycarbonyl)heptyl]-cyclohexene and 5-(t-butylperoxycarbonyl)-4-carboxy-3-pentyl-6-[8-(t-butylperoxycarbonyl)octyl]cyclohexene.

Typical novel di (diacyl peroxides) within the concept of this invention are: 4-acetylperoxycarbonyl-3-hexyl-6-(7-acetylperoxycarbonylheptyl)-cyclohexene, 5-acetylperoxycarbonyl-3-hexyl-6-(7-acetylperoxycarbonylheptyl)cyclohexene, 4-acetylperoxycarbonyl-3-pentyl-6-(8-acetylperoxycarbonyloctyl)cyclohexene, 5-acetylperoxycarbonyl-3-pentyl-6-(8-acetylperoxycarbonyloctyl)cyclohexene, 2-acetylperoxycarbonyl-1-hexyl-4-(7-acetylperoxycarbonylhelpty)cyclohexane, 3-acetylperoxycarbonyl-1-hexyl-4-(7-acetylperoxycarbonylheptyl)cyclohexane, 8-acetylperoxycarbonyl-1-pentyl-4-(9-acetylperoxycarbonyloctyl)cyclohexane, 3-acetylperoxycarbonyl-1-pentyl-4-(8-acetylperoxycarbonyloctyl)cyclohexane, 4-lauroylperoxycarbonyl-3-hexyl-6-(7-lauroylperoxycarbonylheptyl)cyclohexene, 5-lauroylperoxycarbonyl-3-hexyl-6-(7-lauroylperoxycarbonylheptyl)cyclohexene, 4-lauroylperoxycarbonyl-3-pentyl-6-(8-lauroylperoxycarbonyloctyl)cyclohexene, 5-lauroylperoxycarbonyl-3-pentyl-6-(8-lauroylperoxycarbonyloctyl)cyclohexene, 2-lauroylperoxycarbonyl-1-hexyl-4-(7-lauroylperoxycarbonylheptyl)cyclohexane, 3-lauroylperoxycarbonyl-1-hexyl-4-(7-lauroylperoxycarbonylheptyl)cyclohexane, 2-lauroylperoxycarbonyl-1-pentyl-4-(8-lauroylperoxycarbonyloctyl)cyclohexane, 3-lauroylperoxycarbonyl-1-pentyl-4-(8-lauroylperoxycarbonyloctyl)cyclohexane, 4-acetylperoxycarbonyl-3-hexyl-4-methyl-6-(7-acetylperoxycarbonylheptyl)cyclohexene, 2-acetylperoxycarbonyl-1-hexyl-2-methyl-4-(7-acetylperoxycarbonylheptyl)cyclohexane, 4-lauroylperoxycarbonyl-3-hexyl-4-methyl-6-(7-lauroylperoxycarbonylheptyl)cyclohexene, 2-lauroylperoxycarbonyl-1-hexyl-2-methyl-4-(7-lauroylperoxycarbonylheptyl)cyclohexane, 4-isopropoxycarbonylperoxycarbonyl-3-hexyl-6-(7-isopropoxycarbonylperoxycarbonylheptyl)cyclohexene, 5-isopropoxycarbonylperoxycarbonyl-3-hexyl-6-(7-isopropoxycarbonylperoxycarbonylheptyl)cyclohexene, 4-isopropoxycarbonylperoxycarbonyl-3-pentyl-6-(8-isopropoxycarbonylperoxycarbonyloctyl)cyclohexene, 5-isopropoxycarbonylperoxycarbonyl-3-pentyl-6-(8-isopropoxycarbonylperoxycarbonyloctyl)cyclohexene, 2-isopropoxycarbonylperoxycarbonyl-1-hexyl-4-(7-isopropoxycarbonylperoxycarbonylheptyl)cyclohexane, 3-isopropoxycarbonylperoxycarbonyl-1-hexyl-4-(7-isopropoxycarbonylperoxycarbonylheptyl)cyclohexane, 2-isopropoxycarbonylperoxycarbonyl-1-pentyl-4-(8-isopropoxycarbonylperoxycarbonyloctyl)cyclohexane, 3-isopropoxycarbonylperoxycarbonyl-1-pentyl-4-(8-isopropoxycarbonylperoxycarbonyloctyl)cyclohexane, 4-isopropoxycarbonylperoxycarbonyl-3-hexyl-4-methyl-6-(7-isopropoxycarbonylperoxycarbonylheptyl)cyclohexene, 2-isopropoxycarbonylperoxycarbonyl-1-hexyl-2-methyl-4-(7-isopropoxycarbonylperoxycarbonylheptyl)cyclohexane, 4-benzoylperoxycarbonyl-3-hexyl-6-(7-benzoylperoxycarbonylheptyl)cyclohexene, 4-naphthoylperoxycarbonyl-3-hexyl-6-(7-naphthoylperoxycarbonylheptyl)cyclohexene, 4-acryloylperoxycarbonyl-3-hexyl-6-(7-acryloylperoxycarbonylheptyl)cyclohexene, 4-undecenoylperoxycarbonyl-3-hexyl-6-(7-undecenoylperoxycarbonylheptyl)cyclohexene, 4-hexadienoylperoxycarbonyl-3-hexyl-6-(7-hexadienoylperoxycarbonylheptyl)cyclohexene, 4-octadecanoylperoxycarbonyl-3-hexyl-6-(7-octadecanoylperoxycarbonylheptyl)cyclohexene, 4-isobutyrylperoxycarbonyl-3-hexyl-6-(7-isobutyrylproxycarbonylheptyl)cyclohexene, 4-acetylperoxycarbonyl-3-hexyl-6-(7-isobutyrylperoxycarbonylheptyl)cyclohexene, 4-isobutyrylperoxycarbonyl-3-hexyl-6-(7-acetylperoxycarbonylheptyl)cyclohexene, 4-acetylperoxycarbonyl-3-hexyl-6-(7-lauroylperoxycarbonylheptyl)cyclohexene, 4-lauroylperoxycarbonyl-3-hexyl-6-(7-acetylperoxycarbonylheptyl)cyclohexene, 4-acetylperoxycarbonyl-3-hexyl-6-(7-isopropoxycarbonylperoxycarbonylheptyl)cyclohexene, 4-isopropoxycarbonylperoxycarbonyl-3-hexyl-6-(7-acetylperoxycarbonylheptyl)cyclohexene, 4-methoxycarbonylperoxycarbonyl-3-hexyl-6-(7-methoxycarbonylperoxycarbonylheptyl)cyclohexene, 4-dodecanoxycarbonylperoxycarbonyl-3-hexyl-6-(7-dodecanoxycarbonylperoxycarbonylheptyl)cyclohexene, 4-octadecanoxycarbonylperoxycarbonyl-3-hexyl-6-(7-octadecanoxycarbonylperoxycarbonylheptyl)cyclohexene, 4-cyclopentoxycarbonylperoxycarbonyl-3-hexyl-6-(7-cyclopentoxycarbonylperoxycarbonylheptyl)cyclohexene, 4-cyclohexoxycarbonylperoxycarbonyl-3-hexyl-6-(7-cyclohexoxycarbonylperoxycarbonylheptyl)cyclohexene, 4-cyclododecanoxycarbonylperoxycarbonyl-3-hexyl-6-(7-cyclododecanoxycarbonylperoxycarbonylheptyl)cyclohexene and mixtures thereof.

This invention also covers compositions consisting of mixtures of unsymmetrical diperoxyesters and unsymmetrical di(diacyl peroxides) and mixtures of unsymmetrical diperoxides which are prepared by reacting an unsymmetrical diacid chloride with a mixture of a monohydroperoxide and a mono peroxyacid in the presence of a base.

In actual practice, mixtures of isomeric forms of the component of the present invention are usually produced since mixtures of the corresponding isomeric diacids (and subsequently the corresponding isomeric diacid chlorides and diperoxy acids) are usually the precursors.

UTILITY

Ethylenically unsaturated monomers for which compounds of the present invention are useful as initiators include olefins, such as ethylene, propylene, styrene, alpha-methylstyrene, chlorostyrene, vinyltoluene, vinyl benzyl chloride, vinyl pyridine and divinylbenzene; diolefins, such as 1,3-butadiene, isoprene and chloroprene; vinyl esters, such as vinyl acetate, vinyl propionate vinyl laurate, vinyl benzoate and divinyl carbonate; unsaturated nitriles, such as acrylonitrile and methacrylonitrile; acrylic acid, methacrylic acid and their esters and amides, such as methyl, ethyl, n-butyl and 2-ethylhexyl acrylates and methacrylates, and acrylamide and methacrylamide; maleic anhydride; maleic and fumaric acids and their esters; vinyl halo and vinylidene halo compounds, such as, vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, diallyl phthalate, allyl ethyl carbonate, triallyl phosphate, diallyl fumarate and diallyl carbonate; acrolein; methyl vinyl ketone; and mixtures thereof. In such polymerizations, temperatures of 30° C. to 250° C., preferably 40° C. to 200°, and peroxide levels of 0.005 to 3%, preferably 0.01 to 1%, by weight, based on monomer, are normally employed. Polymerization can be carried out in solution where solvents such as benzene may be used. Bulk, solution suspension or emulsion polymerization processes may be employed.

The compound of this invention can also be used to produce high impact polymers such as high impact polystyrene by initiating grafting of the ethylenically unsaturated monomer onto the backbone of elastomers (rubbers) such as polybutadienes, styrene-butadiene-styrene triblock copolymers, ethylene-propylene-diene terpolymers, EPR, etc. The above described vinyl polymerization conditions and initiator levels and up to 15% by weight of rubber (based on monomer) may be used for producing high impact polymers.

The compounds of the present invention are also useful in the curing of unsaturated polyester resin compositions. Such unsaturated polyesters include polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, allylsuccinic acid, tetrahydrophthalic acid and others with saturated or unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl-2-methyl-1,3-propanediol, 2-buten-1,4-diol, 2-butyn-1,4-diol, 2,2,4-trimethyl-1,3-pentanediol, glycerol, pentaerythritol, mannitol and others. Mixtures of such polyacids and/or mixtures of such polyalcohols may also be used. The unsaturated di- or polycarboxylic acids may be replaced, at least partly, by saturated polycarboxylic acids, such as adipic acid, succinic acid, sebacic acid and others and/or by aromatic polycarboxylic acids, such as phthalic acid, trimellitic acid, pyromellitic acid, isophthalic acid and terephthalic acid. The acids used may be halogen-substituted. Examples of such suitable halogenated acids are tetrachlorophthalic acid, 5,6-dicarboxy-1,2,3,4,7,7-hexachlorobicyclo(2.2.1)-2-heptene and others. As a separate component of the unsaturated polyester resin composition includes a polymerizable monomer or monomers such as styrene, chlorostyrene, vinyltoluene, divinylbenzene, alpha-methylstyrene, diallyl maleate, diallyl phthalate, dibutyl fumarate, acrylonitrile, triallyl phosphate, triallyl cyanurate, methyl acrylate, methyl methacrylate, n-butyl methacrylate, ethyl acrylate and others, or mixtures thereof, which are copolymerizable with said polyesters. A preferred resin composition contains as the polyester component the esterification product of 1,2-propylene glycol (a polyalcohol), maleic anhydride (an anhydride of an unsaturated polycarboxylic acid) and phthalic anhydride (an anhydride of an aromatic dicarboxylic acid) as well as the monomer component, styrene. Temperatures of about 20° C. to 200° C. and peroxide levels of about 0.05% to 5% or more by weight of curable unsaturated polyester resin are normally employed. The unsaturated polyesters described above can be filled with various materials such as sulfur, glass fibers, carbon blacks, silicas, metal silicates, clays, metal carbonates, antioxidants, heat and light stabilizers, sensitizers, dyes, pigments, accelerators, metal oxides such as zinc oxide, blowing agents, etc.

The compounds of this invention can also be employed for vulcanizing natural and synthetic rubbers, for curing of olefin copolymers and terpolymers, such as EPR (ethylenepropylene copolymer) and EPDM (ethylene-propylene-diene terpolymer), for crosslinking of PE (polyethylene), ethylene-vinyl acetate copolymers, silicon rubbers, styrene-butadiene rubbers and the like, in the presence or absence of additives and fillers, such as sulfur, carbon blacks, silicas, clays, carbonates, antioxidants, heat and light stabilizers, sensitizers, dyes, accelerators, zinc oxide, oils, blowing agents, etc.

Another use for the compounds of this invention is to produce telechelic polymers having peroxide end groups. In general, the temperature of the monomer polymerization can be controlled so that the lower temperature peroxide moiety of the claimed compound decomposes without appreciable decomposition of the higher temperature peroxide moiety. Since initiator radicals become incorporated into the polymer chains as end groups, some of the polymer molecules will possess end groups containing peroxide functions. Such telechelic polymers may be used to prepare block copolymers by reacting with monomers at suitably high temperatures; self-curing or crosslinking of the telechelic polymer; mill grafting with other polymers; curing agents for resins (e.g. unsaturated polyester) and elastomers; impact modifiers; adhesives; and a variety of other uses which will be apparent to one skilled in the art.

Illustrative Examples

EXAMPLE I

Preparation of a Mixture of 4- and 5-Chlorocarbonyl-3Hexyl-6-[7-(chlorocarbonyl)heptyl]cyclohexenes and 4- and 5- Chlorocarbonyl-3-Pentyl-6-[8-(chlorocarbonyl)octyl]cyclohexenes Westvaco DiAcid 1550 (registered trademark of the Westvaco Corporation) was used to prepare the desired mixture of acid chlorides.

This diacid is produced by reacting linoleic acid with acrylic acid using the well-known Diels-Alder reaction. Apparently, linoleic acid isomerizes to 9,11- and 10,12-octadecadienoic acids prior to reaction with acrylic acid (the dienophile). The Diels-Alder reaction produces a mixture of 4- and 5-carboxyl-3-hexyl-6-(7-carboxyheptyl)cyclohexenes and 4- and 5-carboxy-3-pentyl-6-(8-carboxyoctyl)cyclohexenes. According to the product literature, a structure of Westvaco DiAcid 1550 is illustrated which corresponds to 4-carboxyl-3-hexyl-6-(7-carboxyheptyl)cyclohexene. However, it should be noted that Westavaco DiAcid 1550 is the mixture described above.

To a 1000 ml jacketed reactor equipped with a mechanical stirrer, a thermometer and a condenser with a drying tube was charged 214 g (1.56 moles) of $PCl_3$. To the stirred $PCl_3$ at 45° C. was added 704 g (2.00 moles) of Westvaco DiAcid 1550 over a period of about 30 minutes. The resulting mixture was then stirred for three hours at 45°–50° C., then it was allowed to cool down and separate into phases over a 16 hour period. After separation of the lower phosphorous acid layer, 763 g of liquid diacid chloride was obtained which had a purity of 98.6% based on chloride content. The corrected yield was 96.7%. Future reference to the diacid chloride Muture from Westvaco DiAcid 1550 will be to 4-chlorocarbonyl-3-hexyl-6-(7-chlorocarbonylheptyl)-cyclohexene. It should be understood that such mixture contains 4- and 5-chlorocarbonyl-3-hexyl-6-(7-chlorocarbonyl heptyl)cyclohexenes and 4- and 5-chlorocarbonyl-3-pentyl-6-(8-chlorocarbonyloctyl)cyclohexenes, i.e., the mixture of isomeric chlorides produced from Westvaco DiAcid 1550.

EXAMPLE II

Preparation of a Mixture of 4- and 5-(t-Butylperoxycarbonyl)-3-Hexyl-6 -[7-(t-Butylperoxycarbonyl)heptyl]cyclohexenes and 4- and 5-(t-Butylperoxycarbonyl)-3-Pentyl-6-[8-(t-Butylperoxycarbonyl)octyl]cyclohexenes (C-1)

A jacketed reactor equipped with a mechanical stirrer, a thermometer and a dropping funnel was charged with 700 g of deionized water, 600 g (4.81 moles) of 45% KOH and 468 g (3.61 moles) of 69.5% t-butyl hydroperoxide at 15° to 20° C. To this vigorously stirred solution at 7° to 10° C. was slowly added a solution consisting of 478 g (1.23 moles) of 4-chlorocarbonyl-3-hexyl-6-(7-chlorocarbonylheptyl)cyclohexene and 600 ml of hexane over a period of 45 minutes. The mixture was stirred for 2.0 hours at 10° C. at which time stirring was terminated and the liquid phases were allowed to separate over a period of one hour. The aqueous layer was removed and the organic layer was washed twice with 250 g portions of aqueous 10% KOH solution at 10°–15° C., then with four 450 g portions of aqueous 15% NaCl solution at 10°–15° C. The product solution was then dried with anhydrous MgSO4 and after separation of the desiccant by filtration the solvent was removed in vacuo at 10°–15° C. leaving 390 g of yellow liquid product. The purity of the product based on perester "active oxygen" content (5.79%) was 89.9% whereas the corrected yield was 58.2%. The the product from this example will be referred to hereafter as 4-(t-butylperoxycarbonyl)-3-hexyl-6-[7-(t-butylperoxycarbonyl)heptyl]cyclohexene or composition "C-1".

Decomposition data showed that composition C-1 decomposed at two different rates. The lower temperature peroxide function had a ten hour-half life temperature of 76° C. whereas the higher temperature peroxide function had a ten hour half-life temperature of 97° C.

EXAMPLE III

Preparation of Mixtures of 4- and 5-(t-Alkylperoxycarbonyl)-3-Hexyl-6-[7-(t-Alkylperoxycarbonyl)heptyl]cyclohexenes and 4- and 5-(t-Alkylperoxycarbonyl)-3-Pentyl-6-[8-(t-Alkylperoxycarbonyl)octyl]cyclohexenes Using the conditions of Example II several other 4-(t-alkylperoxucarbonyl)-3-hexyl-6-[7-(t-alkylperoxycarbonyl)heptyl]cyclohexenes were prepared using 4-chlorocarbonyl-3-hexyl-6-[(7-chlorocarbonyl)heptyl]cyclohexene (see Example I) as the diacid chloride and various t-alkyl hydroperoxides as the hydroperoxide. Yield data for the products, including the yield data for composition C-1 are summerized in Example III Table. The designation, 4-(t-alkylperoxycarbonyl)-3-hexyl-6-[7-(t-alkyl peroxycarbonyl)heptyl]cyclohexene, used in the title of Example III Table refers to the isomeric mixture.

EXAMPLE III TABLE

Preparation of 4-(t-Alkylperoxycarbonyl)-3-Hexyl-6-[7-(t-Alkylperoxycarbonyl)heptyl]cyclohexenes

| t-Alkyl Hydroperoxide | Product Obtained | Assay, %* | Corr. Yield, % |
|---|---|---|---|
| t-Butyl hydroperoxide (From Example V) | 4-(t-Butylperoxycarbonyl)-3-hexyl-6-[7-(t-butylperoxycarbonyl)heptyl]-cyclohexene (C-1) | 89.9 | 58.2 |
| t-Amyl hydroperoxide | 4-(t-Amylperoxycarbonyl)-3-hexyl-6-[7-(t-amylperoxycarbonyl)heptyl]-cyclohexene (C-2) | 91.6 | 64.4 |
| 1,1,3,3-Tetramethylbutyl hydroperoxide | 4-(1,1,3,3-Tetramethylbutylperoxycarbonyl)-3-hexyl-6-[7-(1,1,3,3-tetramethylbutylperoxycarbonyl)-heptyl]cyclohexene (C-3) | 85.6 | 49.8 |
| α-Cumyl hydroperoxide | 4-(α-Cumylperoxycarbonyl)-3-hexyl-6-[7-(α-cumylperoxycarbonyl)heptyl]-cyclohexene (C-4) | 81.8 | 19.1 |
| 3-Hydroxy-1,1-dimethylbutyl-hydroperoxide | 4-(3-Hydroxy-1,1-dimethylbutyl-peroxycarbonyl)-3-hexyl-6-[7-(3-hydroxy-1,1-dimethylbutylperoxy-carbonyl)heptyl]cyclohexene (C-5) | 92.5 | 42.3 |
| 1,1,4,4-Tetramethyl-4-(t-butyl-peroxy)outyl hydroperoxide | 4-(1,1,4,4-Tetramethyl-4-(t-butyl-peroxy)butylperoxycarbonyl)-3-hexyl-6-[7-(1,1,4,4-tetramethyl-4-(t-butylperoxy)butylperoxycarbonyl)-heptyl]cyclohexene (C-6) | 94.3 | 70.3 |

*Assay based on "active oxygen" content.

EXAMPLE IV

Preparation of Di-t-butyl 2,2-Dimethyldiperoxysuccinate (C-7)

2,2-Dimethylsuccinyl dichloride was prepared by reacting 2,2-dimethylsuccinic acid with $PCl_5$ in the presence of a solvent at 20° C. After the work-up a yellow liquid was obtained which had a purity of 97.5% according to chloride content. The corrected yield was 67.8%.

A jacketed reactor equipped with a mechanical stirrer, a thermometer and a dropping funnel was charged with 180 g (0.45 mole) of aqueous 10% NaOH solution and 58.3 g (0.45 mole) of 69.5% t-butyl hydroperoxide and the solution was cooled to 0°–5° C. To this solution at 0°–5° C. was added a solution of 100 ml of diethyl ether and 37.6 g (0.20 mole) of 97.5% 2,2-dimethylsuccinyl dichloride over a period of 30 minutes. The reaction mixture was then stirred at 0°–5° C. for 3.0 hours after which 100 ml of diethyl ether was added, stirring was stopped and the aqueous layer was discarded. The organic layer was then washed twice with 50 ml portions of aqueous 10% NaOH, then once with 50 ml of aqueous 10% NaHSO$_3$, then with wate to neutral, all at 0°–10° C. After drying over anhydrous NgSO$_4$ and separation of the desiccant the diethyl ether was removed in vacuo leaving 33.2 g of liquid product. The purity of the product was 97.5% based on perester "active oxygen" content (10.75%). The corrected yield was 55.8%.

EXAMPLE V

Preparation of Dl-t-Butyl n-Octyldiperoxysuccinate (C-8)

n-Octylsuccinyl dichloride was prepared by reacting n-octylsuccinic anhydride with PCl$_5$ at 105°–110° C. for about four hours. After working the product up 101.3 g of liquid was obtained which had a purity of 84.3% according to chloride content. The corrected yield was 79.2%.

A jacketed reactor equipped with a mechanical stirrer, a thermometer and a dropping funnel was charged with 80 g of water, 87.5 g (0.70 mole) of 45% KOH solution and 77.0 g (0.59 mole) of 69.5% t-butyl hydroperoxide. The resulting stirred solution was held at 20°–25° C. while a solution of 80 ml of diethyl ether and 66.5 g (0.21 mole) of 84.3% n-octylsuccinyl dichloride was added slowly over a period of 10 minutes. The resulting mixture was stirred for one hour at 25°–28° C. after which about 150 ml of diethyl ether and 150 ml of water were added, the stirring was stopped and the aqueous layer was discarded. At 20° C. the product layer was washed twice with 150 ml portions of aqueous 20% KOH, once with a 150 ml portion of aqueous 10% NaHSO$_3$ and once with a 150 ml portion of aqueous 5% Na$_2$CO$_3$. After drying over anhydrous MgSO$_4$ and separation of the desiccant by filtration diethyl ether was removed in vacuo leaving 20.7 g of liquid produced. The assay of the product according to perester "active oxygen" content was 93.3% and the corrected yield was 24.6%.

EXAMPLE VI

Preparation of a Mixture of 2- and 3-Chlorocarbonyl-1-Hexyl-4[7-(Chlorocarbonyl)heptyl]cyclohexanes and 2- and 3-Chlorocarbonyl-1-Pentyl-4[8-(Chlorocarbonyl)octyl]cyclohexanes Hydrogenated Westvaco DiAcid 1550, i.e., a mixture of 2- and 3-carboxy-1-hexyl-4-(7-carboxyheptyl)cyclohexanes and 2- and 3-carboxy-1-pentyl-4-(8-carboxyoctyl)cyclohexane was added to a jacketed reactor equipped with a thermometer, a mechanical stirrer and a condenser, charged with 12 g (0.087 mole) of PCl$_3$ and 50 ml of methylene chloride and heated to reflux (ca. 42° C.). A solution of 22.6 g (0.064 mole) of the hydrogenated diacid in 100 ml of methylene chloride was added to the refluxing solution over a period of 15 to 20 minutes. The resulting mixture was refluxed for 3 hours after which stirring was stopped and the reaction mixture was allowed to settle overnight. The lower phosphorous acid layer was separated and discarded. Excess PCl$_3$ and methylene chloride were removed in vacuo at room temperature leaving 22.6 g of liquid product which had an assay of 72.2% according to chloride analysis. The corrected yield was 65.4%. In subsequent experiments the this acid chloride mixture will be referred to as 2-chlorocarbonyl-1-hexyl-4-[7-(chlorocarbonyl)heptyl]cyclohexane.

EXAMPLE VII

Preparation of a Mixture of 2- and 3-(t-Butylperoxycarbonyl)-1-Hexyl-4[7-(t-Butylperoxycarbonyl)heptyl]-cyclohexanes and 2- and 3-(t-Butylperoxycarbonyl)-1-Pentyl-4-[8-(t-Butylperoxycarbonyl)octyl]cyclohexanes (C-9)

Employing the procedure in Example II 2-chlorocarbonyl-1-hexyl-4-[7-(chlorocarbonyl)heptyl]cyclohexane was reacted with t-butyl hydroperoxide, in the presence of aqueous KOH, to give the resulting diperoxyester mixture in 84.4% assay and 84.4% corrected yield. For the sake of simplicity this diperoxyester mixture will be referred to as composition "C-9".

EXAMPLE VIII

Preparation of a Mixture of 2- and 3-(t-Amylperoxycarbonyl)-1-Hexyl-4[7-(t-Amylperoxycarbonyl)heptyl]-cyclohexanes and 2- and 3-(t-Amylperoxycarbonyl)-4-Pentyl-4-[8-(t-Amylperoxycarbonyl)octyl]cyclohexanes (C-10)

Employing the procedure outlined in Example II 2-chlorocarbonyl-1-hexyl-4-[7-(chlorocarbonyl)heptyl]cyclohexane was reacted with t-amyl hydroperoxide, in the presence of aqueous KOH, to give the corresponding diperoxyester mixture in 74.2% assay and 71.9% corrected yield. For the sake of simplicity this diperoxyester mixture will be referred to as composition "C-10".

EXAMPLE VIIIa

Preparation of a Mixture of 4,5-Dichlorocarbonyl-3-Hexyl-6-[7-(Chlorocarbonyl)heptyl]cyclohexene and 4,5-Dichlorocarbonyl-3-Pentyl-6-[8-(Chlorocarbonyl)octyl]cyclohexene A sample of triacid mixture consisting of 4,5-dicarboxy-3-hexyl-6-(7-carboxyheptyl)cyclohexene and 4,5-dicarboxy-3-pentyl-6-(8-carboxyoctyl)cyclohexene obtained from Westvaco Corporation. This triacid mixture was produced by reacting isomerized linoleic acid with fumaric acid according to the Diels-Alder reaction.

A jacketed reactor equipped with a thermometer, a mechanical stirrer and a condenser was charged with a solution of 79.3 g (0.20 mole) of the above triacid mixture in 150 g of methylene chloride. Ten drops of N,N-dimethylformamide (DMF) were added. To this solution at 25° C. to 30° C. was added 85.7 g (0.72 mole) of thionyl chloride over a period of about 25 minutes. The solution was then refluxed for 5 hours at 48° C. to 50° C. after which the solution was cooled to 25° C. and the volatiles (methylene chloride and excess thionyl chloride) were removed in vacuo to give 86 g of liquid which contained 15.1% hydrolyzable chloride (theoretical chloride=23.5%). Since the purity was low (according to chloride content) 77.2 g of the product was treated with 1.0 g of DMF and 164 g (1.38 moles) of thionyl chloride and the solution was refluxed for 5 hours at 75° C. to 80° C. The excess thionyl chloride was then removed in vacuo at 50° C. to 60° C. leaving 88.3 g of liquid product which had a purity of 84.3% according to a hydrolyzable chloride content of 19.8%. The corrected yield was 91.8%. This product is the isomer mixture containing 4,5-dichlorocarbonyl-3-hexyl-6-[7-(chlorocarbonyl)heptyl]cyclohexene in future examples.

EXAMPLE VIIIb

Preparation of a Mixture of
4,5-Di-(t-Butylperoxycarbonyl)-3-Hexyl-6-[7-(t-Butylperoxycarbonyl)heptyl]cyclohexene and
4,5-Di-(t-Butylperoxycarbonyl)-3-Pentyl-6-[8-(t-Butylperoxycarbonyl)octyl]cyclohexene (C-11)

Employing essentially the same procedure used in Example II, 4,5-dichlorocarbonyl-3-hexyl-6-[7-(chlorocarbonyl)heptyl]cyclohexene (see Example VIIIa) was reacted with t-butyl hydroperoxide, in the presence of aqueous KOH, to give the corresponding triperoxyester mixture in 79.2% assay and 46.4% corrected yield. The product was a viscous liquid. This product mixture will be referred to hereafter as 4,5-di-(t-butylperoxycarbonyl)-3-hexyl-6-[7-(t-butylperoxycarbonyl)heptyl]cyclohexene.

EXAMPLE VIIIc

Preparation of a Mixture of
4,5-Di-(t-Amylperoxycarbonyl)-3-Hexyl-6-[7-(t-Amylperoxycarbonyl)heptyl]cyclohexene and
4,5-Di-(t-Amylperoxycarbonyl-3-Pentyl-6-[8-(t-Amylperoxycarbonyl)octyl]cyclohexene (C-12)

Employing essentially the same procedure used in Example II 4,5-dichlorocarbonyl-3-hexyl-6-[7-(chlorocarbonyl)heptyl]cyclohexene (see Example VIIIa) was reacted with t-amyl hydroperoxide, in the presence of aqueous KOH, to give the corresponding triperoxyester mixture (a viscous liquid) in 77.9% assay and 47.5% corrected yield. This product mixture is designated hereafter as 4,5-di-(t-amylperoxycarbonyl)-3-hexyl-6-[7-(t-amylperoxycarbonyl)heptyl]cyclohexene.

EXAMPLE VIIId

Preparation of a Mixture of
3-Hexyl-6-[7-(Chlorocarbonyl)heptyl]cyclohexene-4,5-Dicarboxylic Anhydride and
3-Pentyl-6-[8-(Chlorocarbonyl)octyl]cyclohexene-4,5-Dicarboxylic Anhydride When an attempt was made to prepare the triacid chloride mixture of Example VIIId by reacting the Westvaco triacid mixture (see Example VIIIa for the composition of the triacid mixture) was PCl₃, a mixture of chlorocarbonyl-dicarboxylic anhydrides was actually obtained.

A jacketed reactor equipped with a thermometer, a mechanical stirrer and a condenser was charged with 33 g (0.24 mole) of PCl₃. The PCl₃ was heated to 40° C. and to it was slowly added a solution consisting of 79.3 g (0.20 mole) of Westvaco triacid and 150 g of methylene chloride. The resulting mixture was refluxed at 45° C. for 3.0 hours after which stirring was stopped and the mixture was allowed to separate into two liquid phases over a period of 14 hours at 20° C. The upper product layer was then removed and excess PCl₃ and methylene chloride solvent were removed in vacuo leaving 78 g of liquid product. An infrared spectrum of the product showed the presence of a cyclic anhydride carbonyl band at about 1850 cm$^{-1}$ and a combination acid chloride-cyclic anhydride carbonyl band (very strong) at about 1780 cm$^{-1}$. Little or no free carboxylic acid groups were present as judged by the absence of a carboxylic acid OH band in the infrared spectrum. The hydrolyazable chloride content of the product was 8.50% compared to a theoretical chloride content of 8.93%, therefore, the purity of the title mixture was 85.2% and the corrected yeild was 93.5%. This product was designated 3-hexyl-6-[7-(chlorocarbonyl)heptyl]cyclohexene-4,5-dicarboxylic anhydride.

EXAMPLE VIIIe

Preparation of a Mixture of
4-(t-Butylperoxycarbonyl)-5-Carboxy-3-Hexyl-6-[7-(t-Butylperoxycarbonyl)heptyl]cyclohexene,
5-(t-Butylperoxycarbonyl)-4-Carboxy-3-Hexyl-6-[7-(t-Butylperoxycarbonyl)heptyl]cyclohexene,
4-(t-Butylperoxycarbonyl)-5-Carboxy-3-Pentyl-6-[8-(t-Butylperoxycarbonyl)octyl]cyclohexene and
5-(t-Butylperoxycarbonyl)-4-Carboxy-3-Pentyl-6-[8-(t-Butylperoxycarbonyl)octyl]cyclohexene (C-13)

A jacketed reactor equipped with a mechanical stirrer, a thermometer and a dropping funnel was charged with 31 g of water and 24.9 g (0.20 mole) of 45% KOH solution. To this solution at 20° C. to 25° C. was added 19.4 g (0.15 mole) of 69.5% t-butyl hydroperoxide over a period of 15 minutes. The resulting stirred solution was cooled to 0° C. to 5° C. and to it were added 100 ml of diethyl ether and, over a period of 15 minutes, 20.7 g (0.05 mole) of 95.2% of 3-hexyl-6-[7-(chlorocarbonyl)heptyl]cyclohexene-4,5-dicarboxylic anhydride (see Example VIIId). The resulting mixture was stirred for 2 hours at 5° C. to 10° after which 100 ml of 10% aqueous NaHSO₃ solution was slowly added at 0° C. to 5° C. in order to destroy excess t-butyl hydroperoxide. Then the aqueous layer was separated. The product layer was then washed with 100 ml of water and with 100 ml of saturated NaCl solution. The product was then dried over anhydrous MgSO₄, the desiccant was separated by filtration and the diethyl ether was removed in vacuo at 0° C. to 10° leaving 24.5 g of liquid product. The assay of the product was 54.7% according to "active" oxygen content and the corrected yield was 49.6%. This product mixture was designated 4-(t-butylperoxycarbonyl)-5-carboxy-3-hexyl-6-[7-(t-butylperoxycarbonyl)heptyl]cyclohexene.

EXAMPLE VIIIf

Preparation of a Mixture of
4-(t-Amylperoxycarbonyl)-5-Carboxy-3-Hexyl-6-[7-(t-Amylperoxycarbonyl)heptyl]cyclohexene,
5-(t-Amylperoxycarbonyl)-4-Carboxy-3-Hexyl-6-[7-(t-Amylperoxylcarbonyl)heptyl]cyclohexene,
4-(t-Amylperoxycarbonyl)-5-Carboxy-3-Pentyl-6-[-(t-Amylperoxylcarbonyl)octyl]cyclohexene and
5-(t-Amylperoxycarbonyl-4-Carboxy-3-Pentyl-6-[8-(t-Amylperoxycarbonyl)octyl]cyclohexene (C-14)

Employing the procedure of Example VIIIe 3-hexyl-6-[7-(chlorocarbonyl)heptyl]cyclohexene-4,5-dicarboxylic anhydride (see Example VIIId) was reacted with t-amyl hydroperoxide, in the presence of aqueous KOH, to give the corresponding product mixture in 53.0% essay and 44.4% corrected yield. This product was designated 4-(t-amylperoxycarbonyl)-5-carboxy-3-hexyl-6-[7-(t-amylperoxycarbonyl)heptyl]cyclohexene.

EXAMPLE IX

SPI Exotherma of the Composition of this Invention

The unsaturated polyester resin in this example was a mixture of an unsaturated polyester and styrene monomer. The unsaturated polyester was an alkyd resin made by esterifying the following components:

| Component | Quantity |
|---|---|
| Maleic Anhydride | 1.0 mole |
| Phthalic anhydride | 1.0 mole |
| Propylene glycol | 2.2 moles |

To the resulting resin was added 0.13% by weight of hydrocuinone inhibitor. The alkyd resin had an Acid No. of 45–50. Seven (7) parts by weight of the above polyesters (alkyd resin) was diluted with three (3) parts by weight of monomeric styrene. The resulting unsaturated polyester resin has the following properties:

| | | |
|---|---|---|
| a. | Viscosity (Brookfield No. 2 at 20 r.p.m.) | 13.08 poise |
| b. | Specific Gravity | 1.14 |

CURING PROCEDURE

Gelation and cure characteristics of various initiators in the above unsaturated polyester resin were determined using the Standard SPI Exotherm Procedure ("SPI Procedure for Running Exotherm Curves-Polyester Resins", published in the Preprint of the 16th Annual Conference—Reinforced Plastics Division, Society of the Plastics Industry, Inc., February, 1961). Using the curing procedure described above at 100° C. C-1, an unsymmetrical diperoxyester of this invention, and t-butyl perbenzoate, i.e., "A-6" (a commerical curing catalyst for unsaturated resins) were employed as curing catalysts for this unsaturated polyester resin. The results are summarized below and show that C-1 is considerably more active than A-6.

| | 100° C. SPI Exotherms (1.0% By Wt. Catalyst) | | | |
|---|---|---|---|---|
| Catalyst | Gel, Mins.. | Cure, Mins. | Peak, °F. | Barcol |
| C-1 | 2.6 | 3.6 | 394 | 40–45 |
| A-6 | 10.9 | 13.4 | 404 | 40–45 |

EXAMPLE X

Mold Curing of Unsaturated Polyester Resins

The unsaturated polyester resin described in Example IX was employed in this example. To 60 parts by weight of the resin was added 0.5 parts by weight of zelec UN (An organic release acent). Then 35 parts by weight of ASP-400 (hydrous aluminum silicates) and 5 parts by weight of $TiO_2$ were mixed into the resin for 15 minutes. This gave the molding resin. Prior to mold curing 0.6% by weight of the curing catalyst was blended into the molding resin. During the molding operation, two layers of glass mats were employed to reinforce the cured molding resin. The cured laminate was then composed of 28% by weight of glass mat and 72% by weight of molding resin.

MOLD CURING PROCEDURE

One layer of glass mat was placed in the mold. The molding resin containing 0.6% by weight of catalyst was then weighed onto a second glass mat which was then placed in the mold. A 30 mil fiberglass surface mat was then placed in the mold. A thermocouple was placed between the two glass mats and the press was closed. The laminates were cured at 275° F., or 300° F. and at a mold pressure of 735 p.s.i. (25 tons) on the laminates. The cure time, the peak exotherm and the Barcol hardness were determined by the procedures used in Example IX. The platen gel time was obtained by placing about 5 g of the molding resin onto the hot lower mold surface at the molding temperature and observing the time required to gel the molding resin.

Using the above molding procedure at 275° F. and 300° F. C-1, a composition of this invention, and a 1 to 1 mixture of t-butyl perbenzoate (A-6) and t-butyl peroxy-2-ethylhexoate (available commercially as t-butyl peroctoate) (A-8) were evaluated as curing catalysts for the molding resin. Cure times are summarized below and show that C-1 has cure times at 275° F. and 300° F. which are similar to those of a 1 to 1 mixture of A-6 and A-8.

| | 275° F. and 300° F. Mold Curing | |
|---|---|---|
| Catalyst | Temp., °F. | Cure, Min. |
| C-1 | 275 | 0.63 |
| A-6/A-8 | 275 | 0.50 |
| C-1 | 300 | 0.43 |
| A-6/A-8 | 300 | 0.35 |

EXAMPLE XI

Styrene Polymerizations

An 18 mm×150 mm Pyrex test tube was charged with 5.0 g of distilled styrene and the desired level of free-radical catalyst. The test tube was then chilled in ice water, the vapor space above the styrene solution was purged with dry nitrogen gas and the test tube was sealed with a flame.

The sealed test tube was then immersed in an oil bath. The temperature was then increased continuously over the period of the polymerization.

A short-hand designation of a typical time-temperature profile that could be employed for these styrene polymerizations is as follows:

$$80°\ C.\ \xrightarrow{1\ hr.}\ 120°\ C.\ \xrightarrow{1\ hr.}\ 135°\ C.\ \xrightarrow{1\ hr.}\ 145°\ C.$$

This describes a polymerization that starts (Time=0) at 80° C., one hour is required to continuously increase the temperature to 120° C., then another hour is required to continuously increase the temperature to 135° C., and another hour is required to continuously increase the temperature to 145° C. Hence, the total polymerization time is 3 hours and the temperature employed is 80° C. to 145° C.

After completion of the polymerization the test tube was removed from the oil bath and was quickly chilled in a freezer in order to prevent post-polymerization. After thirty minutes the test tube was removed from the freezer, the tube was broken and the contents were dissolved in 50 ml of benzene containing 0.01 g of benzoquinone (a polymerization inhibitor). This solution was gas chromatographically analyzed for residual styrene. The percent conversion of styrene monomer to polymer was determined by subtracting percent residual styrene from 100%.

The polystyrene produced was isolated by adding the polystyrene/benzene solution to 300 ml of methanol followed by filtration and drying of the precipitated polymer.

The viscosity-average molecular weight ($\overline{M}_v$) of the resulting polymer was determined from viscosity data. The viscosity of a benzene solution of the resulting polystyrene was determined at 25° C. using a Cannon-Ubbelohde viscometer. Extrapolation of the viscosity data to zero concentration, in the usual manner, gave the intrinsic viscosity, [N]. $\overline{M}_v$ was calculated by using the relationship:

$$[N] = K\overline{M}_v^a$$

where $K = 9.18 \times 10^{-5}$ deciliter/g and $a = 0.743$ for polystyrene in benzene at 25° C. [J. Phys. Chem., 67, 566 (1963)].

The molecular weight distribution of the polymer was determined by obtaining a gel permeation chromatogram of the resulting polystyrene and comparing it with the gel permeation chromatograms of polystyrene samples of known narrow molecular weight distribution. A computer with an appropriate program was used to calculate the number-average molecular weight ($\overline{M}_n$) and the weight average molecular weight ($\overline{M}_W$) of the resuling polystyrene.

The molecular weight distribution curve obtained by use of gel permeation chromatography also determined whether the polymer had one or several molecular weight peaks. If only one peak was observed the polymer was considered to have a unimodal molecular weight distribution. If two peaks were observed, the polymer had a bimodal molecular weight distribution. If three peaks were observed, the polymer had a trimodal molecular weight distribution.

and C-12), two commercial initiator systems (0.25 PHW of dibenzoyl peroxide) (A-5) and 0.05 PHW of t-butylperbenzoate (A-6) or 0.25 PHW of A-5 and 0.05 PHW of 2,5-dimethyl-2,5-dibenzoylperoxyhexane (A-9)) and three unsymmetrical diperoxyesters of the prior art or similar to the prior art (di-t-butylmethyldiperoxysuccinate (A-2), C-7 and C-8)) were employed. The results showed that the compositions of this invention (C-1, C-6, C-9 and C-12) gave styrene polymers with much higher molecular weights than did the commercial combination initiator systems or the unsymmetrical diperoxyesters of or similar to the prior art when the novel time-temperature processes or more conventional processes are employed. It should be noted that the unsymmetrical tiperoxyesters of or similar to the art (A-0, C-7 and C-8) gave much lower polystyrene molecular weights (M) than did the compositons of this invention. The results cannot be rationalized on the basis of the prior art. It should be noted that the number of carbon atoms between the two peroxyester functions are greater in the case of the initiator compositions. However, the polystyrene molecular weight results from U.S. Pat. No. 3,585,176 for A-2 (di-t-butyl alphamethyldiperoxysuccinate) and for di-t-butyl alpha, gammadimethyldiperoxyadipate (A-3) were the same (248,000) even though the latter unsymmetrical diperoxyester (A-3) had two more carbon atoms than A-2 in the alkylene group between the two peroxyester functions.

It is also interesting to note that the use of two of the compositions of this invention, (C-1 and C-6) resulted in polystyrenes having unimodal molecular weight distribution (see Example XI Table) although unsymmetrical di- and polyperoxides of the art have been reported to give bimodal or trimodal polystyrene molecular weight distributions. Therefore, the styrene polymers resulting from use of the art unsymmetrical di- or polyperoxides have extremes in molecular weight distributions. This is detrimental to strength and moldability of the resulting

EXAMPLE XI TABLE

STYRENE POLYMERIZATIONS

| Initiator System | Level, PHM | Time-Temp. Profile | % Conv. | Polystyrene Molecular Weight × 10$^{-5}$ | | | $M_w/M_n$ | Molecular Weight* Distribution |
| --- | --- | --- | --- | --- | --- | --- | --- | --- |
| | | | | $\overline{M}_v$ | $\overline{M}_w$* | $\overline{M}_n$* | | |
| C-1 | 0.25 | 1 | 98.8 | 2.50 | 3.55 | 1.27 | 2.80 | Unimodal |
| C-6 | 0.25 | 1 | 99.6 | 2.99 | 3.81 | 1.31 | 2.91 | Unimodal |
| A-5 / A-6 | 0.25 / 0.05 | 1 | 99.9 | 1.61 | — | — | — | Unimodal** |
| A-5 / A-9 | 0.25 / 0.05 | 1 | 99.9 | 1.51 | — | — | — | — |
| C-7 | 0.25 | 2 | 93.8 | 1.63 | — | — | — | — |
| A-2 | 0.25 | 2 | 99.9 | 1.52 | — | — | — | — |
| C-9 | 0.25 | 2 | 93.2 | 1.85 | — | — | — | — |
| C-12 | 0.25 | 2 | 89.7 | 1.76 | — | — | — | — |
| C-8 | 0.25 | 2 | 96.2 | 1.65 | — | — | — | — |
| C-1 | 0.25 | 2 | 99.9 | 1.91 | — | — | — | — |
| C-1 | 0.30 | CONV | 99.1 | 2.97 | — | — | — | — |
| A-5 / A-6 | 0.25 / 0.05 | CONV | 99.9 | 1.85 | — | — | — | — |

Time-Temp. Profile 1: 80° C. $\xrightarrow{1\,hr.}$ 100° C. $\xrightarrow{1\,hr.}$ 115° C. $\xrightarrow{1\,hr.}$ 125° C. $\xrightarrow{1\,hr.}$ 135 ⓡ C. $\xrightarrow{1\,hr.}$ 140° C.

Time-Temp. Profile 2: 80° C. $\xrightarrow{1\,hr.}$ 120° C. $\xrightarrow{1\,hr.}$ 135° C. $\xrightarrow{1\,hr.}$ 145° C.

Time-Temp. profile CONV: 4 hours at 90° C. then 4 hours t 120° C.
*Obtained from gel permeation chromatography data.
**According to the polystyrene industry.

Example XI Table summarizes data from styrene polymerizations in which several unsymmetrical diperoxyester compositions of this invention (C-1, C-6, C-9 polystyrenes. Commercial polystyrene produced using the commercial initiator system (e.g., mixtures of A-6 and A-5) result in polystyrene having unimodal molecular weight distribution according to reports from the polystyrene industry.

EXAMPLE XII

Methyl Methacrylate Solution Polymerizations

An 18 mm×150 mm Pyrex test tube was charged with 2.0 g of distilled methyl methacrylate (MMA), 6.0 g of 4-butyrolactone (solvent) and the desired level of free-radical catalyst or catalyst system. The test tube was then chilled in ice water, the vapor space above the methyl methacrylate solution was purged with dry nitrogen gas and the test tube was sealed with a flame.

The sealed test tube was then immersed in an oil bath. The temperature of the oil bath was then increased continuously over the period of the solution polymerization.

The same time-temperature profiles as used in Example XI for styrene polymerizations were used in this example.

After completion of the polymerization the test tube was removed from the oil bath and was quickly cooled in a freezer in order to prevent post-polymerization. The test tube was then broken and the contents were dissolved in about 115 ml of 4-butyrolactone. The 4-butyrolactone solution was then added slowly to 2 liters of vigorously stirred methanol to precipitate the poly(-methylmethacrylate) (PMMA). The PMMA was then separated by filtration and was dried overnight in a 50° C. vacuum oven. The weight of the PMMA was obtained and the percent conversion of MMA to PMMA was determined.

The viscosity average molecular weight ($\overline{M}_v$) of the resulting PMMA was determined at 25° C. using a Cannon-Ubbelohoe viscometer. Extrapolation of the viscosity data to zero concentration, in the usual manner, gave the intrinsic viscosity, [N]. $\overline{M}_v$ was calculated by employing the relationship:

$$[N] = K\overline{M}_v{}^a$$

where $K = 5.5 \times 10^{-5}$ deciliter/g and $a = 0.76$ for PMMA in benzene at 25° C. [H. J. Cantow and G. V. Schulz, Z. Physik Chem. 1, 365 (1954) and 2, 117 (1954)].

Example XII Table summarizes data from MMA solution polymerizations in which the time-temperature profile was:

60° C. 1 hr. 80° C. 1 hr. 90° C. 1 hr. 100° C. 1 hr. 110° C. 1 hr. 120° C.

The catalysts used were a mixture of 0.25 PHM of dibenzoyl peroxide (A-5) and 0.05 PHM of t-butyl peroxybenzoate (A-6) and 0.30 PHM of C-1, an unsymmetrical diperoxyester composition of this invention. The results in Example XII Table show that use of C-1 gives PMMA with much higher viscosity average molecular weight ($\overline{M}_v$) than does the commercial initiator system (A-6 and A-5).

EXAMPLE XII TABLE

METHYL METHACRYLATE SOLUTION POLYMERIZATIONS

| Initiator System | Level PHM | Time-Temp. Profile | % Conv. | PMMA Molecular Weight ($\overline{M}_v$)×10$^{-5}$ |
|---|---|---|---|---|
| A-5 | 0.25 } | 3 | 90.3 | 1.387 |
| A-6 | 0.05 | | | |
| C-1 | 0.30 | 3 | 90.5 | 2.503 |

Time-Temp. Profile 3: 60° C. $\xrightarrow{1\,hr.}$ 80° C. $\xrightarrow{1\,hr.}$ 90° C. $\xrightarrow{1\,hr.}$ 100° C. $\xrightarrow{1\,hr.}$ 110° C. $\xrightarrow{1\,hr.}$ 120° C.

EXAMPLE XIII

High Impact Styrene Polymerizations

To 25.0 g of distilled styrene was added 1.25 g (4.8%) of elastomer and the resulting mixture was stirred until solution occurred. An 18 mm×150 mm Pyrex test tube was then charged with 5.0 g of the above styrene solution and the desired level of free-radical grafting catalyst. The test tube was chilled, the vapor space above the styrene-elastomer solution was purged with dry nitrogen and the test tube was sealed with a flame.

The sealed test tube was immersed in an oil bath and the temperature of the oil bath was then continuously increased over the period of the high impact styrene polymerization.

The same time-temperature profiles as used in Example XI for styrene polymerizations were used in this example.

After completion of the polymerization the test tube was removed from the oil bath and was quickly cooled in a freezer in order to prevent post-polymerization. The test tube was then broken, the polymer was broken into several pieces and the polymer was added to 50 ml of benzene containing 0.01 g of benzoquinone (a polymerization inhibitor). The mixture was stirred for one day at room temperature in order to insure that all of the soluble polystyrene was dissolved by the benzene. The polymer that was insoluble in benzene (i.e., the gel) was further sectioned with a spatula. The gel was then removed from the benzene-polystyrene solution and was washed twice with about 40 ml portions of benzene and the benzene washings were combined with the benzene-polystyrene solution. The volume of the benzene swollen gel was then measured, then the gel was placed in 50° C. vacuum oven. The dried gel was then weighed.

The soluble polystyrene was then precipitated by adding the benzene-polystyrene solution to two liters of vigorously stirred methanol. The precipitated polystyrene was separated by filtration, dried in a 50° C. vacuum oven and weighed. The percent conversion was determined from the weight of the dried gel, the dried soluble polystyrene and the weight of the starting styrene-elastomer solution. The following equations were employed for determining various properties of the high impact polystyrene produced:

$$\% \text{ Conv.} = 100 \left( \frac{\text{wt. dry gel} + \text{wt. dry soluble polystyrene}}{\text{wt. styrene} - \text{elastomer solution}} \right)$$

$$\% \text{ Gel} = \frac{100 \,(\text{wt. dry gel})}{\text{wt. styrene} - \text{elastomer solution}}$$

$$\% \text{ Graft} = \frac{100 \,(\% \text{ gel} - \% \text{ elastomer})}{100 - \% \text{ elastomer}}$$

-continued

% Graft Polystyrene = % gel − % elastomer

Graft/Rubber Ratio = % Grafted Polystyrene / % elastomer

The viscosity average molecular weight ($\overline{M}_v$) of the soluble polystyrene was determined by the method outlined in Example XI.

Example XIII Table summarizes the high impact styrene polymerization data obtained when C-1, and a commercial initiator system (A-5 and A-6) were employed. The time-temperature profile employed was:

80° C. 1 hr. → 100° C. 1 hr. → 115° C. 1 hr. → 125° C. 1 hr. → 135° C. 1 hr. → 140° C.

Two elastomers were employed:
(1) Kraton 101—Shell Chemical Company A polystyrene-polybutadiene-polystyrene triblock copolymer containing 30% by weight of styrene.
(2) Taktene 1202—Polymer Corporation Ltd. A high cis-1,4-polybutadiene rubber containing about 98% cis-, 1% trans-and 1% vinyl-butadiene units.

The results in Example XIII Table show that use of C-1, brought about greater grafting of polystyrene onto Kraton 101 and Taktene 1202 than occurred when the commercial initiator system (A-5 and A-6) was employed. This conclusion was based on the results for the % gel, graft, % grafted polystyrene and the graft/rubber ratio. Greater grafting of styrene onto the backbone of elastomers is advantageous commercially since more high impact polystyrene is produced in a given batch of high impact polystyrene, thus less crystalline polystyrene is produced. Hence, the polystyrene manufactured has greater impact resistance. Furthermore, the initiators of this invention can be used with less elastomer to produce an impact polystyrene with the same impact resistance. Thus, the same impact resistance can be obtained using less of the more expensive elastomer and more of the less expensive styrene monomer.

It is interesting to note that the soluble polystyrene produced using C-1 as the initiator had a much higher $\overline{M}_v$ than did the soluble polystyrene produced using the commmercial initiator system (A-5 and A-6). These results were similar to those obtained in Example XI.

EXAMPLE XIV

Preparation of a Mixture of 4- and 5-Lauroyl-peroxycarbonyl-3-Hexyl-6-(7-Lauroylperoxycarbonylheptyl)cyclohexenes and 4- and 5-Lauroylperoxycarbonyl-3-Pentyl-6-)8-Lauroylperoxycarbonyloctyl)cyclohexenes (C-15)

A jacketed reactor equipped with a mechanical stirrer, a thermometer and a dropping funnel was charged with 100 ml of diethyl ether, 4.75 g (0.06 mole) of pyridine and 14.2 g (0.06 mole) of peroxylauric acid (93.3%). The resulting solution was cooled to 0° C. and to this vigorously stirred solution at 0° to 5° C. was added 14.0 g (0.03 mole) of 4-chlorocarbonyl-3-hexyl-6-(7-chlorocarbonylheptyl)cyclohexene (83%) over a period of 15 minutes. The mixture was then stirred for 2.0 hours at 0° to 5° C. Then 50 ml of cold water was added and the organic layer was separated from the aqueous layer. The organic layer was washed with two 25 ml portions of 7% $H_2SO_4$, then with two 50 ml portions of 10% $Na_2CO_3$/10% NaCl solution and then with 100 ml of 10% NaCl solution. The product solution was then dried over anhydrous $MgSO_4$ and after separation of the spent desiccant by filtration the solvent was removed in vacuo at 0° to 5° C. leaving 20.4 g of an amber liquid. The purity of the product was 73.3% based on "active oxygen" content. The corrected yield was 66.5%.

This product (C-15) was evaluated as a curing catalyst for the unsaturated polyester resin composition that was described in Example IX. The temperature employed was 82° C. and the level of C-15 used was equal in "active oxygen" content to 1% by weight of t-butyl peroxypivalate, a commercial low temperature peroxide. The results are summarized in the table below:

| Catalyst | 82° SPI Exotherms | | | |
| --- | --- | --- | --- | --- |
| | Gel. Mins. | Cure, Mins | Peak, °F. | Barcol |
| t-Butyl Peroxyplyalate | 1.2 | 2.1 | 382 | 40–45 |
| C-15 | 0.8 | 1.9 | 357 | 25–30 |

The results show that C-15 was more active in the unsaturated polyester resin composition than was t-butyl peroxypivalate.

EXAMPLE XIII TABLE

HIGH IMPACT STYRENE POLYMERIZATIONS

| Initiator System | Level, PHM | Elastomer Used* | % Conv. | Soluble Polystyrene $\overline{M}_v \times 10^{-5}$ | % Gel | % Graft | % Grafted Polystyrene | Graft/ Rubber Ratio |
| --- | --- | --- | --- | --- | --- | --- | --- | --- |
| A-5 | 0.25 | Kraton 101 | 100 | 1.76 | 24.0 | 20.2 | 19.2 | 4.0/1.0 |
| A-6 | 0.05 | | | | | | | |
| C-1 | 0.30 | Kraton 101 | 100 | 2.66 | 32.0 | 28.6 | 27.2 | 5.7/1.0 |
| A-5 | 0.25 | Taktene 1202 | 100 | 1.75 | 40.0 | 37.0 | 35.2 | 7.3/1.0 |
| A-6 | 0.05 | | | | | | | |
| C-1 | 0.30 | Taktene 1202 | 100 | 2.52 | 49.0 | 46.4 | 44.2 | 9.2/1.0 |

*4.8% by wt. elastomer employed.

Time-Temp. Profile: 80° C. 1 hr. → 100° C. 1 hr. → 115° C. 1 hr. → 125° C. 1 hr. → 135° C. 1 hr. → 140° C.

EXAMPLE XV

Preparation of a Mixture of 4- and 5-Acetylperoxycarbonyl-3-Hexyl-6-(7-Acetylperoxycarbonylheptyl)cyclohexenes and 4- and 5-Acetylperoxycarbonyl-3-Pentyl-6-(8-Acetylperoxycarbonyloctyl)cyclohexenes (C-16)

Employing essentially the same procedure as used in Example XIV, 4-chlorocarbonyl-3-hexyl-6-(7-chlorocarbonylheptyl)cyclohexene (85.7%) was reacted with 20.8% peroxyacetic acid (in ethyl acetate) in the presence of pyridine. The product mixture was obtained in an assay of 61.3% and a corrected yield of 50.8%.

We claim:

1. Unsymmetrical diperoxides of the structure

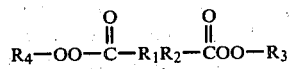

$$R_4-OO-\overset{O}{\underset{\|}{C}}-R_1R_2-\overset{O}{\underset{\|}{C}}OO-R_3$$

where $R_1$ is a substituted or unsubstituted cyclohexylene or cyclohexenylene diradical, $R_2$ is an alkylene diradical of 7 to 11 carbons, alkenylene diradical of 9 to 11 carbons or an alkadienylene diradical of 11 carbons, $R_3$ and $R_4$ can be the same or different and are substituted or unsubstituted acyl radicals of 1 to 18 carbon atoms, alkenoyl radicals of 3 to 11 carbons, alkadienoyl radicals of 6 carbons, hydrocarbon-aroyl radicals of 7 to 11 carbons, alkoxycarbonyl radicals of 2 to 19 carbons and cycloalkoxycarbonyl radicals of 6 to 13 carbons wherein substituents for $R_1$ are selected from one or more alkyl radicals of 1 to 6 carbons, alkenyl radicals of 4 to 6 carbons, alkadienyl radicals of 6 carbons, —C(O)OOR_3, —C(O)OOR_4 and carboxy, and the substituents for $R_3$ and $R_4$ are selected from lower alkyl.

2. A di(diacyl peroxide) and a di(diacyl peroxide) mixture according to claim 1 wherein said acyl group is lauroyl.

3. A di(diacyl peroxide) and a di(diacyl peroxide) mixture according to claim 1 wherein said acyl group is acetyl.

4. A di(diacyl peroxide) according to claim 1 which selected from 4-(acylperoxycarbonyl)-3-hexyl-6-(7-acylperoxycarbonylheptyl)cyclohexene, 5-(acylperoxycarbonyl)-3-hexyl-6(7-acylperoxycarbonylheptyl)cyclohexene, 4-(acylperoxycarbonyl)-3-pentyl-6-(8-acylperoxycarbonyloctyl)cyclohexene and 5-(acylperoxycarbonyl)-3-pentyl-6-(8-acylperoxycarbonyloctyl)cyclohexene and mixtures thereof.

5. A di(diacyl peroxide) according to claim 1 which selected from 4-(aroylperoxycarbonyl)-3-hexyl-6-(7-aroylperoxycarbonylheptyl)cyclohexene, 5-(aroylperoxycarbonyl)-3-hexyl-6-7-aroylperoxycarbonylheptyl)cyclohexene, 4-(aroylperoxycarbonyl)-3-pentyl-6-(8-aroylperoxycarbonyloctyl)cyclohexene and 5-(aroylperoxycarbonyl)-3-pentyl-6-(8-aroylperoxycarbonyloctyl)cyclohexene and mixtures thereof.

* * * * *

UNITED STATES PATENT AND TRADEMARK OFFICE
CERTIFICATE OF CORRECTION

PATENT NO. : 4,219,676
DATED : August 26, 1980
INVENTOR(S) : J. Sanchez, V. R. Kamath, J. C. Halas It is certified that error appears in the above—identified patent and that said Letters Patent is hereby corrected as shown below:

In column 24, line 25 reads

"peroxycarbonyl)-3-hexyl-6-7-aroylperoxycarbonylhep-"

It should read

-- peroxycarbonyl)-3-hexyl-6-(7-aroylperoxycarbonylhep- --.

Signed and Sealed this

Second Day of December 1980

[SEAL]

Attest:

SIDNEY A. DIAMOND

Attesting Officer

Commissioner of Patents and Trademarks